United States Patent [19]

Horner et al.

[11] 4,260,829

[45] Apr. 7, 1981

[54] PREPARATION OF CARBONYL COMPOUNDS

[75] Inventors: Michael Horner, Neustadt; Axel Nissen, Leimen; Peter R. Laurer, Ludwigshafen; Matthias Irgang, Mannheim; Heinrich Pasedach, Weisenheim am Berg, all of Fed. Rep. of Germany

[73] Assignee: BASF Aktiengesellschaft, Fed. Rep. of Germany

[21] Appl. No.: 67,706

[22] Filed: Aug. 17, 1979

[30] Foreign Application Priority Data

Sep. 11, 1978 [DE] Fed. Rep. of Germany ....... 2839474

[51] Int. Cl.$^3$ .............................................. C07C 45/62
[52] U.S. Cl. .................................... 568/462; 568/434; 568/396; 568/318; 260/465 R; 560/51

[58] Field of Search ...................... 260/601 R, 593 R; 568/462

[56] References Cited

U.S. PATENT DOCUMENTS

| 3,860,657 | 1/1975 | Easter et al. ..................... 260/601 R |
| 3,971,830 | 7/1976 | Gradeff ............................ 260/601 R |

*Primary Examiner*—Bernard Helfin
*Attorney, Agent, or Firm*—Keil & Witherspoon

[57] ABSTRACT

Carbonyl compounds $R^1$—$CHR^2$—$CHR^3$—$CR^4O$ (I, $R^1$=H or an organic radical; $R^2$-$R^4$=H or $C_1$–$C_4$-alkyl) are prepared by selective hydrogenation of the $\alpha,\beta$-unsaturated carbonyl compounds $R^1$—$CR^2$=$CR^3$—$CR^4O$ (II) in the liquid phase by means of hydrogen in the presence of a palladium catalyst and of from 15 to 50% by weight, based on (II), of a tertiary amine.

4 Claims, No Drawings

PREPARATION OF CARBONYL COMPOUNDS

The present invention relates to an improved process for the preparation of carbonyl compounds of the general formula I

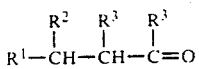

where $R^1$ is hydrogen or an organic radical and $R^2$, $R^3$ and $R^4$ are hydrogen or $C_1$–$C_4$-alkyl, by selective hydrogenation of α,β-unsaturated carbonyl compounds II

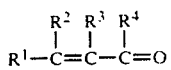

with hydrogen in the presence of a palladium catalyst and an organic base, in the liquid phase.

More particularly, the invention relates to the selective hydrogenation of citral (IIa)

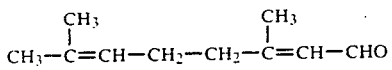

to citronellal (Ia)

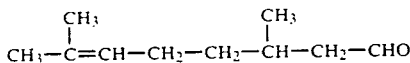

German Published Application No. DAS 2,114,211 discloses the preparation of citronellal (Ia) by hydrogenating citral (IIa) with hydrogen in the presence of a moist palladium catalyst and of a base, in the liquid phase. The bases recommended include organic bases, eg. tertiary amines, in particular in an amount of from 0.1 to 10% by weight, based on citral.

However, the relatively long reaction times of this process are unsatisfactory. It is true that they can be shortened by using larger amounts of the Pd catalyst, but this has the disadvantage that the catalyst costs are increased. Even if the catalyst is not consumed, it does become deactivated in the course of time, and successful regeneration of the catalyst is in general not possible. Technologically, the use of relatively large amounts of catalyst is also disadvantageous because of the problems of handling of solids.

It is an object of the present invention to provide an overall more economical method than hitherto available for hydrogenating the α,β-unsaturated carbonyl compounds (II), particular citral (IIa), to the corresponding α,β-saturated carbonyl compounds (I).

We have found that this object is achieved by an improved process for the preparation of the carbonyl compounds (I) by selective hydrogenation of the carbonyl compounds (II) with hydrogen in the presence of a palladium catalyst and of an organic base, in the liquid phase, wherein the hydrogenation is carried out in the presence of from 15 to 50% by weight, based on (II), of a tertiary amine.

The process according to the invention gives improved results and at the same time allows considerable savings of Pd catalyst, compared to the conventional method, and uses smaller amounts of a basic agent, for example a tertiary amine. Futhermore, the selectively in respect of the products (I) is improved, which is particularly important in the case of scents and aromatics, for example citronellal, since, if the product is purified at economically acceptable expense, the decrease in yield is several times greater than that attributable to the amount of concomitant materials.

According to the observations we have made hitherto, all tertiary amines are suitable in principle, so that their chemical nature is immaterial provided they do not possess other functional groups capable of undergoing other reactions with the reactants present. Examples of suitable tertiary amines are aliphatic tertiary amines of a total of 3 to 30 carbon atoms, especially trimethylamine, as well as triethylamine, triethanolamine and trihexylamine, cyclic tertiary amines, eg. N-methylpiperidine, N-methylmorpholine and N,N'-dimethylpiperazine, aliphatic-cycloaliphatic tertiary amines, eg. N,N-dimethylcylcohexylamine, aliphatic-araliphatic tertiary amines, eg N,N-dimethylbenzylamine, aliphatic-aromatic tertiary amines, eg. N,N-dimethylaniline and heterocyclic-aromatic tertiary amines, eg. pyridine and quinoline.

For economic reasons, it is desirable to use very cheap amines, having a boiling point either substantially lower or substantially higher than that of the desired product, since in such cases either the amine or the product can easily be distilled from the reaction mixture.

The amount of amine used is preferably from 25 to 40% by weight of the starting material (II).

Hydrogenation catalysts which can be used are all conventional palladium catalysts or supported palladium catalysts, especially those using carbon, in the form of carbon black or active carbon, as the carrier. Catalysts supported on active charcoal, and having a surface area of from 600 to 1,000 m²/kg, a pore diameter distribution maximum at from 4 to 50 Angström, and a mean Pd particle size of from 8 to 50 Angström, are particularly suitable. The Pd content of the catalyst is from 0.1 to 50, preferably from 0.5 to 20, % by weight.

Depending on the nature of the starting material (II), the reaction conditions, and the Pd content and physical properties of the catalyst, the latter is required in amounts of from 0.01 to 10% by weight, based on (II). Preferably, relatively small amounts, namely from 0.01 to 1.0% by weight, based on (II), are employed, since in that case one of the essential advantages of the improvement according to the invention, namely the shorter reaction time, is particularly marked.

A further advantage of the process is that the presence of water, which in the prior art is recommended as increasing the selectivity, is no longer essential, though on the other hand water does not interfere but merely, when used in greater amount than 5% by weight of the reaction mixture, slows down the hydrogenation.

On the other hand, it is advisable to carry out the reaction in the presence of a solvent. The amount of solvent is in general from 10 to 300, preferably from 25 to 150, % by weight of (II). Suitable solvents are all inert liquids in which (I) and (II), as well as the tertiary amine used, are soluble. Examples of suitable solvents are the tertiary amines themselves, as well as alcohols, eg. methanol and ethanol, ethers, acetone and hydrocarbons which are liquid under the reaction conditions, eg. hexane and cyclohexane. Methanol is preferred, especially if trimethylamine is used as the base.

In other respects, the hydrogenation is carried out in a conventional manner, i.e. at from 5 to 150° C., under atmospheric or slightly superatmospheric pressure or even at higher pressures of up to about 50, preferably up to about 10, bar.

The process according to the invention is of particular importance for the hydrogenation of citral (IIa) to citronellal (Ia), which is known to present technical problems because of multiple hydrogenation and isomerization.

The process however is equally well applicable to the other compounds defined by the formula (II), and with most of these also offers the advantages mentioned relative to the conventional processes.

The radicals $R^1$ in the compounds (II) can in principle be of any type. If these radicals contain one or more double bonds conjugated with the $\alpha,\beta$-double bond, these also undergo hydrogenation, which may be desirable. If on the other hand, as in the case of (IIa), the double bonds are isolated, they are as a rule not attacked. Equally, the great majority of substituents is not attacked, since even sensitive formyl groups remain intact.

Examples of $R^1$ are alkyl and alkenyl of 1 to 20 carbon atoms and aromatic radicals, eg. phenyl. These radicals can themselves be substituted, for example by alkyl, alkoxy, formyl, carbalkoxy, acyl, hydroxyl, carboxyl, nitrile, amino and halogen.

EXAMPLE 1

Hydrogenation of citral 152 g portions of commercial citral (containing about 145 g of citral) were hydrogenated, in the presence of 1.5 g of a Pd/active charcoal catalyst, under a hydrogen pressure of 1.05 bar, at 20° C. in the presence of a % by weight of trimethylamine and b % by weight of methanol, each percentage being based on citral (145 g=100%), until hydrogen absorption ceased, which occurred after t hours.

The catalyst contained 5% by weight of Pd, the mean diameter of the Pd particles was 45 Angström, the pore diameter distribution maximum of the active charcoal was at 5 Angström and the surface area was 857 m²/g.

The experimental results, determined by distillation and gas chromotography, are shown in the Table which follows.

| Experiment No. | a (% by weight) | b (% by weight) | t (h) | Conversion (%) | Selectivity (%) (based on conversion) | | Residue (g) |
|---|---|---|---|---|---|---|---|
| | | | | | Citronellal | Dimethyl-octanal | |
| Comparative experiments | | | | | | | |
| 1 | 1 | 2.5 | 43 | 65 | 62 | 0.5 | 3 |
| 2 | 2 | 5 | 31 | 100 | 92 | 1.3 | 3 |
| 3 | 4 | 10 | 24 | 100 | 95 | 1.7 | 3 |
| 4 | 8 | 20 | 21 | 100 | 95 | 1.7 | 3 |
| 5 | 10 | 25 | 20 | 100 | 95 | 1.7 | 3 |
| According to the invention | | | | | | | |
| 6 | 20 | 50 | 16 | 100 | 95 | 0.8 | 3 |
| 7 | 30 | 100 | 13 | 100 | 96 | 0.8 | 3 |

As may be seen, the measures taken according to the invention substantially reduce the reaction time and furthermore improve the selectivity.

EXAMPLE 2

Hydrogenation of citral 152 g portions of commercial citral (containing about 145 g of citral) were hydrogenated, in the presence of 0.4 g of a Pd/active charcoal catalyst, under a hydrogen pressure of 6 bar, at 40° C. in the presence of a % by weight of trimethylamine and b % by weight of methanol, each percentage being based on citral (145 g=100%), until hydrogen absorption ceased, which occurred after t hours.

The catalyst contained 5% by weight of Pd, the mean diameter of the Pd particles was 45 Angström, the pore diameter distribution maximum of the active charcoal was at 5 Angström and the surface area was 850 m²/g.

The experimental results, determined similarly to Example 1, are shown in the Table which follows.

| Experiment No. | a (% by weight) | b (% by weight) | t (h) | Conversion (%) | Selectivity (%) (based on conversion) | | Residue (g) |
|---|---|---|---|---|---|---|---|
| | | | | | Citronellal | Dimethyl-octanal | |
| Comparative experiments | | | | | | | |
| 1 | 6 | 12 | 13 | 99 | 97 | 2 | 1.5 |
| 2 | 8 | 16 | 12 | 100 | 97 | 1 | 2.0 |
| According to the invention | | | | | | | |
| 3 | 30 | 60 | 8 | 100 | 97 | 0.5 | 1.5 |
| 4 | 40 | 80 | 6 | 100 | 97 | 0.4 | 1.5 |

Here again, addition of an amine, in accordance with the invention, substantially reduces the reaction time. However, under otherwise identical conditions but using only 10% by weight of amine, such a reduction is only possible with about 10 times the amount of catalyst.

EXAMPLES 3 to 8

Preparation of various carbonyl compounds (I)

145 g portions of an α,β-unsaturated carbonyl compound II were hydrogenated, using 5 g of the catalyst from Example 1, in the presence of 20% by weight of trimethylamine and 40% by weight of methanol, based on the amount of (II), at 40° C. under a hydrogen pressure of 6 bar, until, after t hours, there was no further absorption of hydrogen. The results are shown in the Table which follows.

| Example | Compound (II) | Conversion (%) | t (h) | Product (I) | Selectivity (based on conversion) (%) |
|---|---|---|---|---|---|
| 3 | 6-methylhept-3-en-2-one | 100 | 7 | 6-methylheptan-2-one | 96 |
| 4 | 2-ethylhex-2-en-1-al | 100 | 6 | 2-ethylhexan-1-al | 96 |
| 5 | 2-methylpent-2-en-1-al | 99 | 6 | 2-methylpentan-1-al | 97 |
| 6 | crotonaldehyde | 99 | 8 | butyraldehyde | 90 |
| 7 | 3-methylbut-2-en-1-al | 100 | 8 | 3-methylbutyraldehyde | 93 |
| 8 | p-tert.-butylmethacrolein | 84 | 5 | p-tert.-butylisobutyraldehyde | 86 |

Example 9

Hydrogenation of citral 152 g of commercial citral (citral content about 145 g) were hydrogenated in the presence of 0.2 g of the palladium catalyst from Example 1 and 25% by weight of triethylamine (based on citral) under a hydrogen pressure of 6 bar at 50° C., the hydrogen absorption ceasing after 8 hours. Conventional working up gave 145 g of 97.4% pure citronellal, containing 0.5% of dimethyloctanal. The yield was 96.8%.

We claim:

1. In a process for the preparation of a carbonyl compound of the formula (I)

$$R^1-CH-CH-C=O \atop \phantom{R^1-}|\phantom{CH-CH}|\phantom{CH}| \atop \phantom{R^1-CH-CH-C=}R^2\phantom{-}R^3\phantom{-}R^4 \tag{I}$$

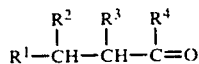

where $R^1$ is alkyl or alkenyl of 1 to 20 carbon atoms and $R^2$ and $R^3$ are hydrogen or $C_1$–$C_4$-alkyl and $R^4$ is hydrogen, by the selective hydrogenation of the α,β-unsaturated carbonyl compound (II)

with hydrogen in the presence of a palladium catalyst, an organic solvent and an organic base, in the liquid phase, the improvement which comprises: carrying out the hydrogenation in the presence of from 15 to 50% by weight, based on (II), of an aliphatic tertiary amine of 3 to 30 carbon atoms, wherein as solvent there is used between 25 and 150% by weight of (II) of methanol or ethanol and wherein the water concentration in the reaction mixture does not exceed 5% by weight.

2. The process of claim 1, wherein the catalyst used is a Pd/active charcoal supported catalyst which has a Pd content of from 0.1 to 50% by weight, a mean diameter of the Pd particles of from 8 to 50 Angström, a pore diameter distribution maximum at from 4 to 50 Angström, and a surface area, of the active charcoal, of from 600 to 1,000 m²/kg.

3. The process of claim 1 or 2, wherein trimethylamine is used as the tertiary amine and methanol is the solvent.

4. The process of claims 1 or 2, wherein citral is hydrogenated to citronellal and wherein trimethylamine is used as the tertiary amine.

* * * * *